United States Patent [19]
Tcherny et al.

[11] Patent Number: 6,082,999
[45] Date of Patent: Jul. 4, 2000

[54] INTERDENTAL DEVICE AND CONTAINER

[76] Inventors: Iosif Tcherny, 9205 Bumble Bee Dr. Unit 1B, Des Plaines, Ill. 60016; Samuel N. Gomon, 1140 W. Northshore Ave., Chicago, Ill. 60626

[21] Appl. No.: 09/361,598

[22] Filed: Jul. 27, 1999

[51] Int. Cl.[7] .................................................. A61C 17/00
[52] U.S. Cl. ............................ 433/80; 433/81; 132/321; 132/308
[58] Field of Search .................................. 433/80, 81, 89, 433/216, 415; 132/321, 308, 309, 311, 329; 206/63.5

[56] References Cited

U.S. PATENT DOCUMENTS

| | | | |
|---|---|---|---|
| D. 293,858 | 1/1988 | Tarrson et al. | D4/104 |
| 4,040,433 | 8/1977 | Edison | 132/321 |
| 4,810,122 | 3/1989 | Cole | 401/122 |
| 4,911,187 | 3/1990 | Castillo | 132/329 |
| 4,922,936 | 5/1990 | Buzzi et al. | 132/329 |
| 5,337,766 | 8/1994 | Lane | 132/327 |
| 5,775,346 | 7/1998 | Szyszkowski | 132/329 |

Primary Examiner—John J. Wilson
Assistant Examiner—Robyn Kieu Doan
Attorney, Agent, or Firm—Paul H. Gallagher

[57] ABSTRACT

A plastic dental article, including an outer container made up of an outer shell and a tubular insert. It also includes a stem having an interdental pick and a brush near the pick but spaced slightly therefrom. The container is non-spill, when turned over, either when the stem is in place therein, or removed therefrom.

7 Claims, 6 Drawing Sheets

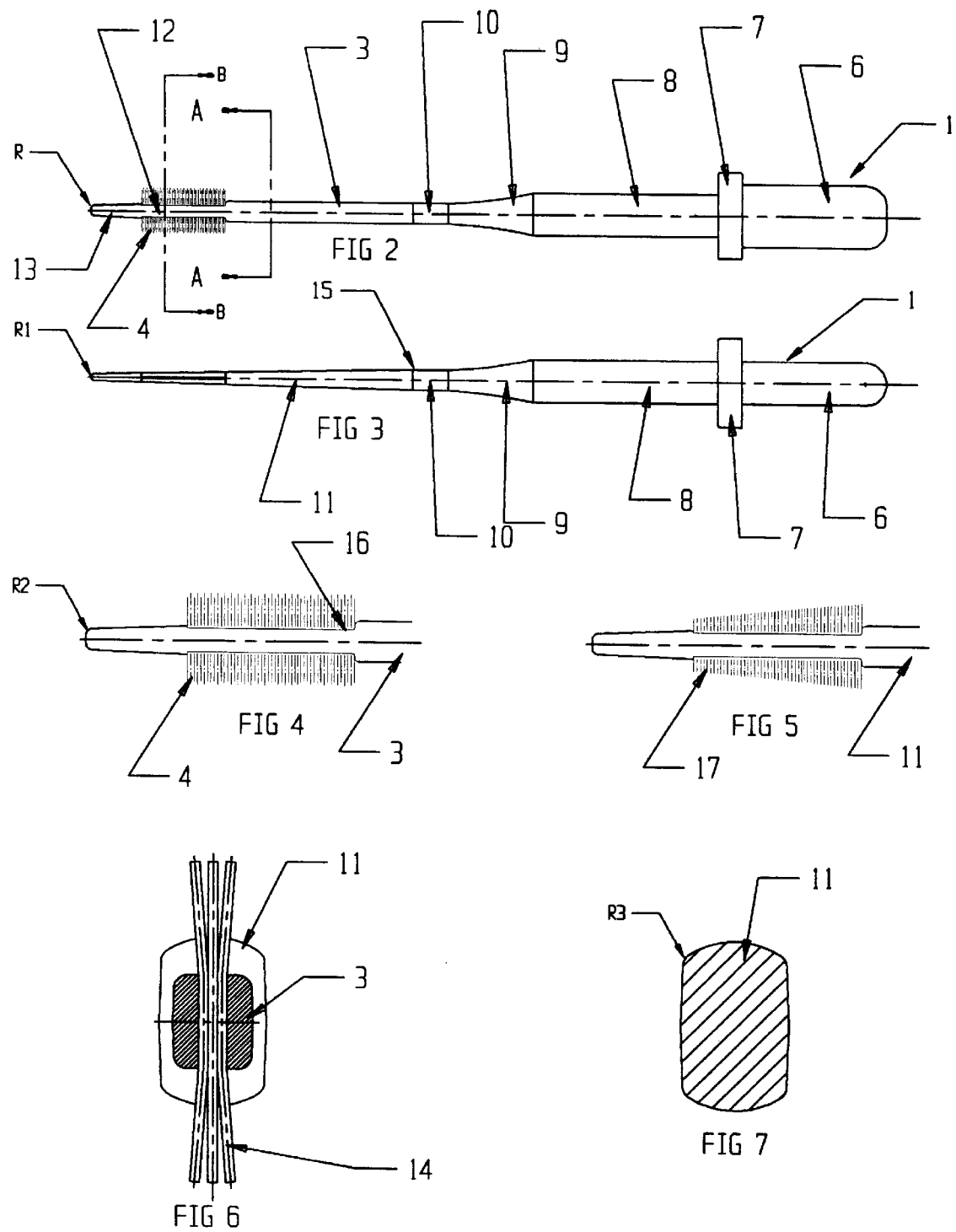

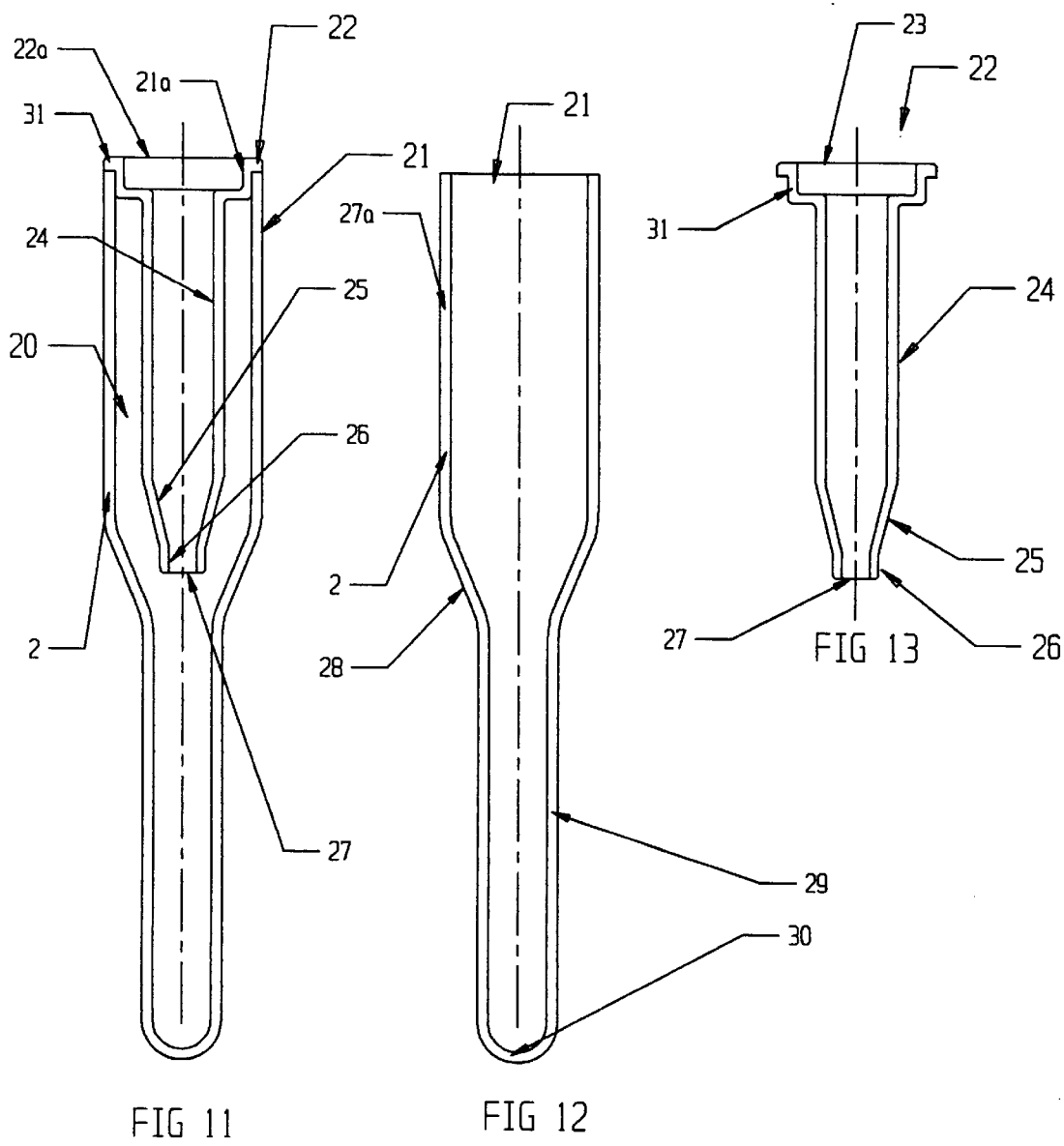

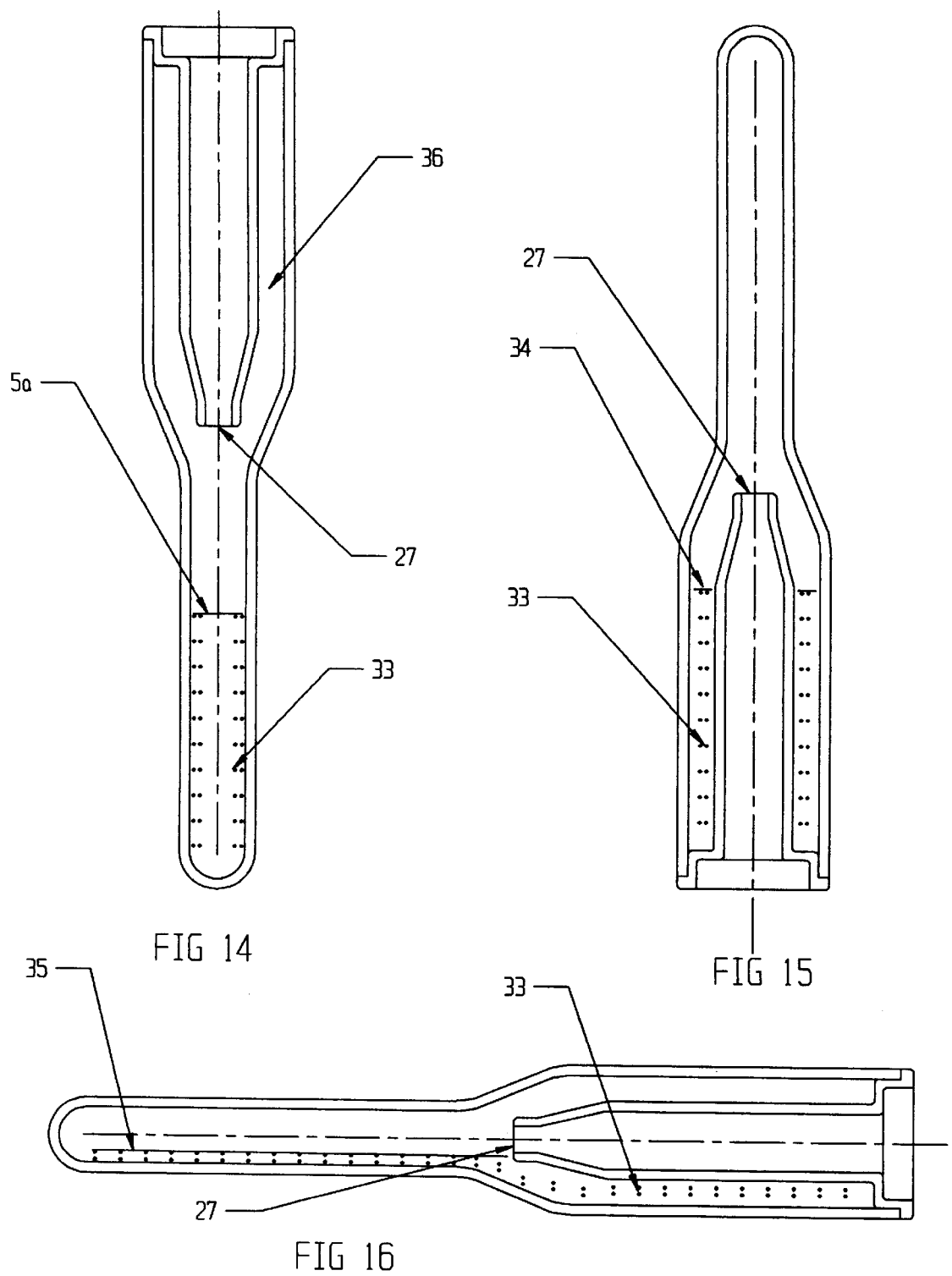

INTERDENTAL DEVICE AND CONTAINER

FIELD OF INVENTION

The present invention relates generally to dental hygiene devices. Particularly, the invention relates to a device which combines advantages of a toothpick and an interdental brush. Additionally the device of the invention includes a container with a liquid therein (such as mouthwash, dental rinse or others) for disinfecting of the interpick brushes after usage, and for applying medication or mouthwash to the teeth and gum.

BACKGROUND OF THE INVENTION

Various devices are known for cleaning and stimulating the teeth and gum to maintain good dental hygiene, such as toothbrushes, gum simulators, floss, toothpicks and interdental brushes.

The present invention comprises a device for cleaning and stimulating the teeth and gum, which combines advantages of interdental brushes and toothpicks, and which includes a non-spill container for holding a liquid for protecting the device from contamination and mechanical damages, and for disinfecting the device after usage, and delivering medication to the gum and teeth with each usage.

Existing toothpicks come in a variety of sizes and shapes, examples of which are found in the following U.S. patents.

U.S. Pat. No. 4,577,649 dated Mar. 25, 1986. The main disadvantage of this and similar devices is that they all serve for cleaning purposes only: to remove remaining particles of food between the teeth, but can not remove the bacteria at the gum as interdental brushes do. Another disadvantage of the toothpicks is that they are not reusable.

U.S. Pat. No. 4,040,433, dated Aug. 9, 1977. This device is a reusable toothpick with an end cap and elongated container which holds the mouthwash. The toothpick is inserted into the container and sealed by the end cap. A disadvantage of this device is that the mouthwash can be easily spilled out if the container drops without the end cap thereon, and the mouthwash liquid can be spilled during transportation if the end cap is disengaged from the container for any reason.

U.S. Pat. No. 5,551,456, dated Sep. 3, 1996, describes a mascara brush. In general, all interdental brushes have the same construction as mascara brushes and are manufactured on the similar equipment. The difference is only in size of the wire, size of the filament and shape of the filament trimming. All presently known interdental brushes have wire structure therein. Disadvantages of the interdental brushes are the following: metal wire is not safe for gum and enamel, because users can get galvanize electrical shock from the wire during usage, and for that reason wire is coated with nylon or other coating to prevent the electrical shock. Equipment for manufacturing of the interdental brushes is expensive and requires high maintenance. Another problem with manufacturing of wire brushes is that coating can be displaced from the wire during twisting operation in the fabrication thereof. Interdental brushes with large diameter wire can not be used safely by the patients with small gaps between the teeth, since wire can destroy the enamel during use. For this reason interdental brushes are made of small wire diameter in order to fit into the tight space between the teeth. But interdental brushes of small wire diameter can be easily bent during usage, and this bending produces a great deal of difficulty for using the brushes.

Another problem with the use of the twisted interdental brushes is that filaments can become loose and fall out during use. Another problem with usage of the interdental brushes is that they should be carefully washed after each application to eliminate possibilities for bacteria grow on the brushes.

Pat. #D293858, dated Jan. 26, 1988 discloses a combined interdental brush and cap. Disadvantages of this construction are similar to those described above for all interdental brushes. The cap in this device serves for brush protection from mechanical damage during transportation.

U.S. Pat. No. 4,810,122, dated Mar. 7, 1989 describes a cosmetic applicator and wiper therefor. The cosmetic container has four pieces in its construction, and can retain therein the viscous or semi-liquid material only when container is closed by the cap. A disadvantage of this device is that the container with a cap of this form can not reliably retain the low viscous liquid from leaking through. This patent also describes the cosmetic applicator with integrally molded bristles. The technology of integrally molded bristles is very well known, and as described in this patent, the bristles in the cosmetic applicator serve for retaining the cosmetic material.

OBJECTS OF THE INVENTION

The object of this invention is to provide a device which combines advantages of the toothpick and interdental brush, and eliminates disadvantages of current devices.

Another object of this invention is to design a convenient device, flexible in two perpendicular directions, which enables the user to reach in a far corner of the mouth, even between the wisdom teeth and the teeth adjacent thereto, without placing the fingers inside the mouth.

Another object of this invention is to provide such a product with a non-spill container for hygiene application.

An additional object of the invention is to provide a reusable, inexpensive product having a long life.

Yet another object of the invention is to design a product which is well adapted to simple fabrication steps.

SUMMARY OF THE INVENTION

The reusable, flexible interdental device with non-spill container providing the following functions:

1) facilitating removal of food particles after every meal;
2) interdental deep cleaning and massaging the gum;
3) dental liquid is applied to the gum and teeth for medical and refreshing purposes, with each usage of the device;
4) cleaning and disinfecting steps for interdental device are performed after each usage.

The device has a removable unit with a rear end forming a handle and front portion in the form of an elongated, flexible thin-wall blade of tapered shape without sharp edges, and with brush filaments molded in its working tip end. This blade forms the toothpick part of the product and is very thin at the working tip, in order to fit into even the narrowest spaces between the teeth. In one of the embodiments of the device, the width at this point is 0.020", and increases in thickness toward the handle in order to increase the strength of the device and provide cleaning effect between the teeth that have bigger gaps. The interdental part of the product includes the brush filaments molded into the thinnest part of the toothpick blade, at the working end. The filaments are disposed perpendicular to the main axis of the blade, and spaced along its length. In order to achieve the interdental cleaning effect desired, the blade is sufficiently rigid in longitudinal direction to withstand the resistance of insertion of the device between the teeth and sufficiently flexible in transverse directions to form a curve of the blade to accommodate positioning of the device relative to the location of the teeth. The filaments of the brush are rigid enough to reach into the gum pocket. For additional benefits of effective cleaning, part of the blade with the filaments are also flexible in the direction perpendicular to the thin dimension of the blade, at its working tip end. In other words, the device provides flexibility in two mutually perpendicular directions in order to effectively perform the task of cleaning and massaging the gum and removing food particles between the teeth. To provide the rigidity of the device the blade is designed as a thin wall rib with significant and substantial ratio of the wall thickness to width in perpendicular directions. In one of the embodiments of the device this ratio is 6. It allows to achieve flexibility in one direction and relative rigidity in perpendicular direction.

To provide flexibility of the overall device, the cross-section of the blade increases smoothly in two perpendicular directions from the thinnest cross-section at the tip to the thickest at the handle end of the blade. To provide the additional flexibility of the device in the direction perpendicular to the thinnest cross-section (in a range of practical plastic deformation without destroying the device) the cross-section of the area with the filaments or bristles is of less cross section area than the remainder of the blade.

Additionally, in order to provide a degree of rigidity of the immediate portion of the blade with the filaments, two factors are incorporated into the design of the filaments; the filaments do not have spaces between them, and the length of the filaments is shorter than, equal to, or not significantly longer than the width of the blade. The container comprises a two parts design. The first part forms the external shell of the container and includes a cylindrical wall having two segments of different diameters with a conical segment therebetween, a closed bottom, and an open top. The second part forms the internal shell of the container, and includes a tubular, open-ended member, having a flange at its outer end for receiving a cap on the interpick part. It also includes two cylindrical segments with a conical segment therebetween.

BRIEF DESCRIPTION OF THE DRAWINGS

The described objects and advantages of the invention will become evident from the following drawings:

FIG. 2 is a side view of the interpick device.

FIG. 3 is another side view of the interpick device, perpendicular to the direction of the view on FIG. 2.

FIG. 4 is a fractional view of the interdental part of the device with filaments of uniform length.

FIG. 5 is a fractional view of the interdental part of the device with tapered shape of the filaments.

FIG. 6 is a sectional view taken at line B—B of FIG. 2, showing the filaments molded in the blade.

FIG. 7 is a sectional view taken at line A—A of FIG. 2.

FIG. 11 is a longitudinal sectional view of the non-spill container.

FIG. 12 is a longitudinal sectional view of the outer part of the container.

FIG. 13 is a longitudinal sectional view of the inner part of the container.

FIGS. 14, 15 and 16 are longitudinal sectional views of the container with liquid therein, in three different positions respectively upright, inverted vertical, and horizontal.

DETAILED DESCRIPTION OF THE DRAWINGS

Figure 1:
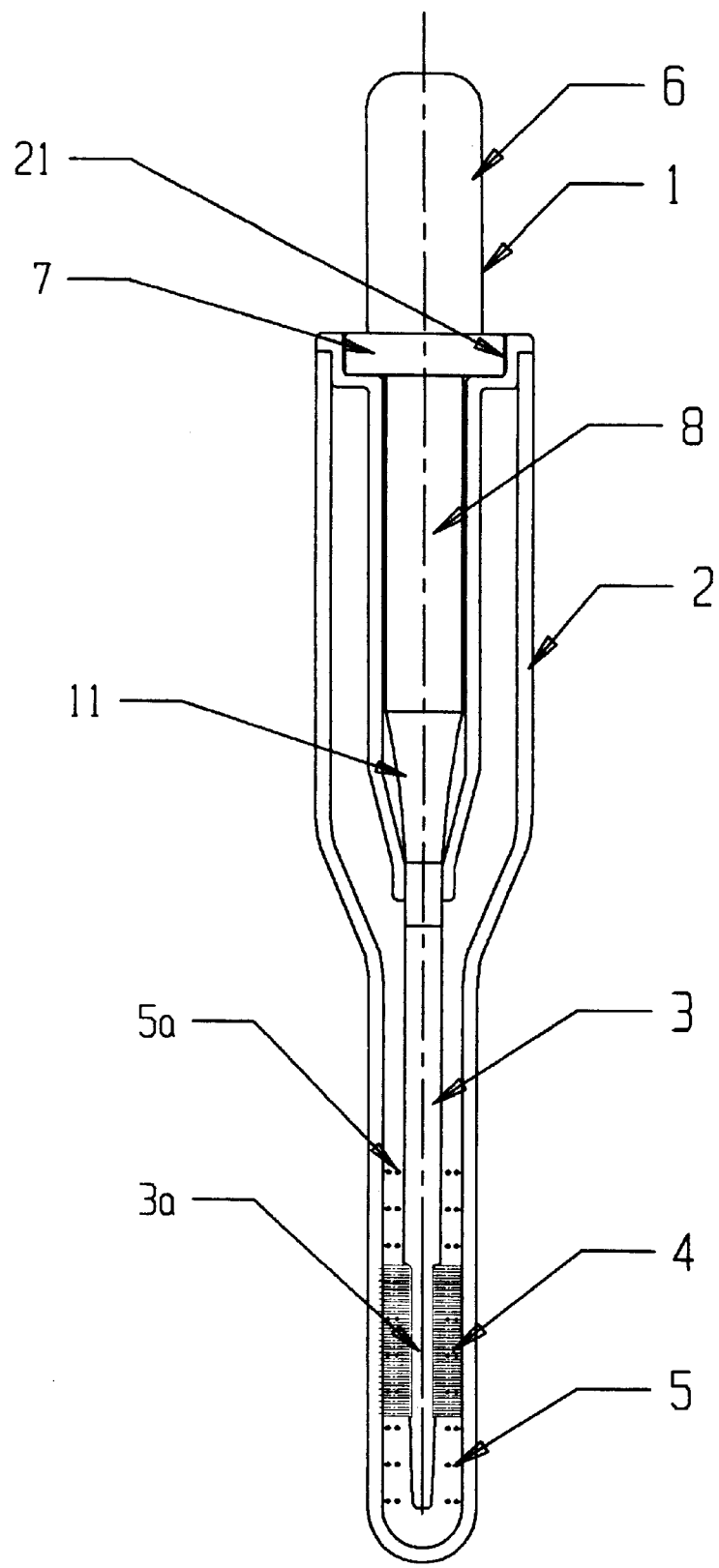
FIG. 1 is a longitudinal sectional view of the device which shows the interpick device placed inside the non-spill container.

FIG. 1 depicts the interpick device 1 assembled in the non-spill container 2. The interpick device or stem 1 consists of a handle 6, a body 8, a blade 3 and filaments 4 molded into the blade 3, and forming a brush. The blade serves as a toothpick. Filaments 4 are molded into the decreased cross-section 3a of the blade 3, which provides interdental function of the device. The container 2 has a quantity of dental liquid 5 therein, reaching a height 5a in FIG. 1 (see also FIGS. 14–16).

The interpick device is formed by injection molding process. The filaments are gripped in the mold, and the molding material is injected thereinto. The material for the stem of the interpick device is plastic and no metal is included in the device.

FIG. 2 depicts the interpick device with straight filaments or bristles 4 of uniform length. The interpick device includes a solid body including a rounded handle 6 with two different dimensions (cf. FIGS. 2 and 3) in mutually perpendicular directions for convenience of handling the device and for convenience in orientation thereof in respect to the cross-section of the blade 3 with filaments 4 during usage. An end cap 7 is molded as an element of the interpick device 1 and engages the inner part of the container (FIG. 11) at the surface 21a. The cylindrical body 8 FIGS. 2, 3 of the interpick device 1 merges into a transitional conic part 9 and cylindrical part 10 and then into the blade and, the blade 3 has cross-section dimensions increasing from the tip 13 of the blade (FIG. 3) to the tail of the blade 3, at 15. The tip 13 is the thinnest part of the blade and at the tail 15 is the thickest part of the blade. In order to provide flexibility of the blade and resistance to collapse during usage, the blade 3 has different dimensions in two perpendicular directions. In one of the embodiments of this device the ratio of the dimensions in two perpendicular directions is 6. It enables achievement of flexibility of the blade in one direction and less flexibility or relative rigidity in perpendicular direction. The blade does not have any sharp corners and can not damage the gum. Radii R, R1, R2 and R3 in FIGS. 2, 3, 4, and 7 show this design.

FIG. 3 is another view of the interpick device. This view is perpendicular to the view of FIG. 2 and shows the thin dimension of the blade.

FIG. 4 illustrates the filaments 4 molded into the decreased thickness section 16 of the blade 3, providing reliable securement of the filaments with the blade. The filaments 4 have no spaces therebetween, and one or several filaments extend through the blade (FIG. 6) of the interpick device. The length of the filaments is shorter than, equal to, or not significantly greater than, the width of the blade. This design provides significant resistance to collapsing of the filaments during usage and provides recovery of its shape after usage. In one form (FIG. 4) the filaments are of uniform length progressing axially. The scope of the invention is such as to cover different lengths of filaments progressing in axial direction.

FIG. 5 illustrates another embodiment of the device, in which the filaments 17 are of progressively decreasing length toward the tip end, forming an overall tapered shape.

FIG. 6 is a cross-sectional view taken at line B—B of FIG. 2, showing the filaments 4 molded in the blade 3, from which it will be seen that the blade is thinner at this location than at any other location. This may be compared with the thickness of the blade at 11 which is shown in section in FIG. 7.

Figure 8:
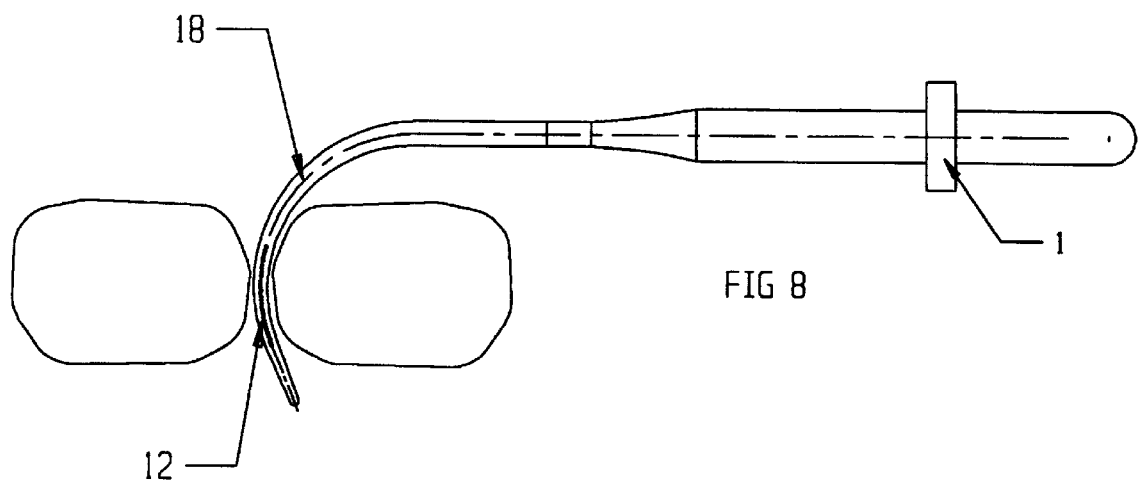
FIG. 8 is a face view of the bent interpick device in cleaning action between the teeth.

FIG. 8 is a side view of the bent interdental device in cleaning action between the teeth. The design of the device allows the device to be bent and recover after usage, to its original shape.

Figure 9:
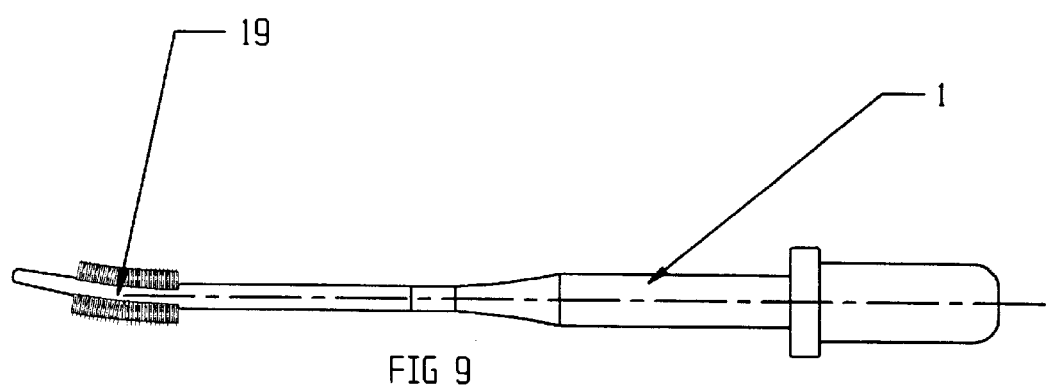
FIG. 9 is face view of the interpick with the filaments therein, slightly bent, and viewed in the direction perpendicular to that of FIG. 8.

FIG. 9 is a side view of the device with bent interdental part, and with the filaments in the direction perpendicular to that in FIG. 8. The design allows the portion 19 of the device to be bent in direction perpendicular to the thin portion of the device.

Figure 10:
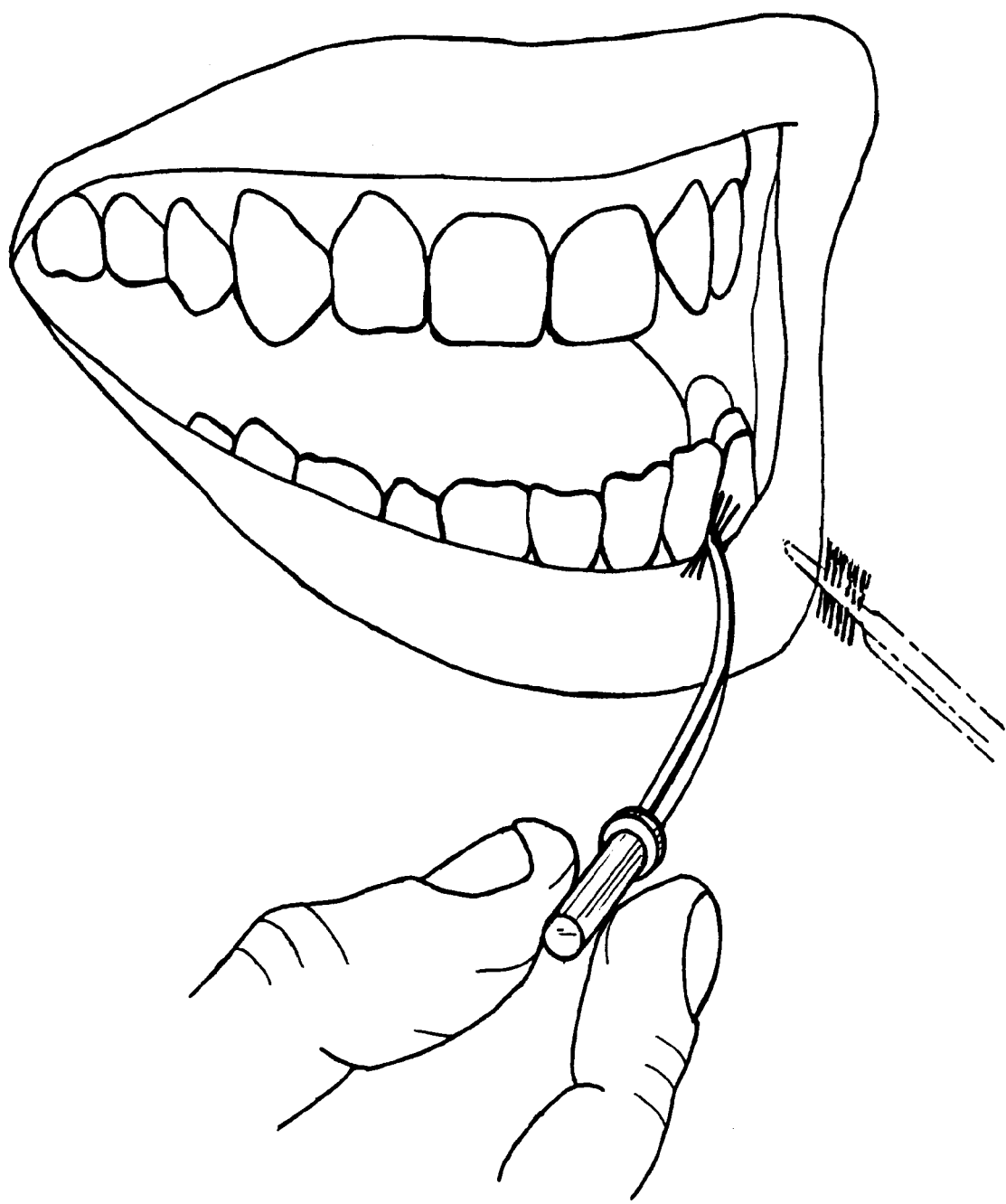
FIG. 10 is a perspective view of the interpick device in action in the corner of the mouth.

FIG. 10 is a perspective view of the interpick device in cleaning position in the corner of the mouth. The design of the device allows it to be bent and to reach in the far corner of the mouth without placing the fingers inside the mouth.

FIG. 11 illustrates the non-spill container 2 (FIG. 1), which consists of two main parts: an outer shell or casing 21 (FIG. 12) and a cylindrical insert 22 (FIG. 13). The outer shell consists of two cylindrical segments 27a, 29 of different diameters, and a conic segment 28 therebetween. The bottom end is closed by a spherical segment 30, and the top is open at 22a.

The insert 22 (FIG. 13) includes a flange 23 at the top, a cylindrical segment 24, a conical segment 25, and a lowermost cylindrical segment 26 which has an open lower end 27.

The main parts 21, 22 are assembled as shown in FIGS. 1 and 11, being secured together at 31. The cleansing liquid 5 is put in the assembled container to the level 5a (FIG. 1). The container is thereby completed.

The interpick device 1 (FIG. 1) is inserted into the assembled container 2 (FIG. 1), with the filaments or brush extending into the liquid, and is withdrawn and used as desired.

When the interpick device 1 (FIG. 1) is in such position in the casing, it is held there by a tight friction fit between the elements at the cylindrical surface 21a (FIG. 11).

The container prevents spilling of the liquid even when the interpick device is not in place in the container. Concerning this feature attention is directed to FIG. 14, 15, and 16 which show the container with the dental liquid therein, in different positions of the container: upright vertical, inverted vertical, and horizontal. The quantity of liquid is so selected that the level thereof is below the opening 27 of the insert 36. In any position of the container, the level of the liquid as shown at 5a, 34, and 35, is below the opening 27 of the insert. Thus the insert is not necessary that the interpick device be in place in the container to prevent spilling; even if the user should drop or put the container down, while holding the interpick device, the liquid would not be spilled.

What is claimed is:

1. A dental device comprising, a container and a stem, the container being adapted for holding a liquid therein and having a fixed opening enabling inserting the stem therethrough while holding the liquid therein, the stem having a front end segment of small cross-sectional dimensions and a rear end, of larger cross-sectional dimensions, and the front end segment decreasing in dimension in forward direction in each of mutually transverse directions, and being flexible in each of said transverse directions, the front end segment including a relatively sharp pick component at its front end, and the front end segment including a brush component rearwardly of the pick component.

2. A dental device according to claim 1 wherein, the front end segment is relatively flat, having a width dimension and a thickness dimension.

3. A dental device according to claim 2 wherein, the stem is of molded material, the brush component including bristles made up of extruded filaments, of uniform diameter extending through and molded in the material of the stem.

4. A dental device according to claim 3 wherein, the bristles extend in the width direction of the front end segment.

5. A dental device according to claim 3 wherein, the filaments are positioned side-by-side in direction axially of the stem, without spaces between next adjacent filaments in that direction.

6. A dental device according to claim 5 wherein, the filaments extend through the stem on both sides of the stem, and the filaments are of sufficiently small number in direction transverse to the blade as to present a generally flat shape of the brush component as viewed axially of the stem.

7. A dental device comprising, a container including an outer casing and an insert, a stem, the outer casing having an open top end and a closed bottom end, and having an upper large portion and a small lower portion joined together adjacent the middle of the outer casing by a conical portion, the casing being adapted to hold a liquid therein, the insert being of lesser transverse dimension than the outer casing, and being open at both its upper and lower ends, the insert being positioned in the outer casing with the upper ends of the insert and outer casing sealed together, and the insert terminating downwardly adjacent the middle of the outer casing, whereby communication is established between the lower portion of the casing and the upper portion thereof surrounding the insert, and the stem is positioned in the container extending through the insert and into the small lower portion of the casing, and the various elements being so positioned and dimensioned that when the container is positioned either in vertically reversed position or lying on a level surface, independently of the presence of the stem in the container, liquid therein when extending up to a predetermined level below the juncture of the casing portions will rise only to a position below the open inner end of the insert, whereby to prevent flow of the liquid out of the container.

* * * * *